United States Patent
Han et al.

(10) Patent No.: US 10,417,388 B2
(45) Date of Patent: Sep. 17, 2019

(54) APPARATUS AND METHOD FOR PROVIDING VIRTUAL TREATMENT EXPERIENCE

(71) Applicant: CHUNG ANG UNIVERSITY INDUSTRY ACADEMIC COOPERATION FOUNDATION, Seoul (KR)

(72) Inventors: Doug Hyun Han, Seoul (KR); Joung Soon Jang, Seoul (KR); In Gyu Hwang, Busan (KR); Hee Jun Kim, Seoul (KR); Byung Doo Choi, Seoul (KR); Jong Deok Kim, Seoul (KR); Hyung Won Cho, Seoul (KR)

(73) Assignee: CHUNG ANG UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 344 days.

(21) Appl. No.: 15/302,689

(22) PCT Filed: Apr. 7, 2015

(86) PCT No.: PCT/KR2015/003441
§ 371 (c)(1),
(2) Date: Oct. 7, 2016

(87) PCT Pub. No.: WO2015/156563
PCT Pub. Date: Oct. 15, 2015

(65) Prior Publication Data
US 2017/0024540 A1    Jan. 26, 2017

(30) Foreign Application Priority Data

Apr. 7, 2014  (KR) .................. 10-2014-0041194

(51) Int. Cl.
*G06F 19/00*     (2018.01)
*G16H 50/30*     (2018.01)
(Continued)

(52) U.S. Cl.
CPC ......... *G06F 19/3456* (2013.01); *G06Q 10/10* (2013.01); *G06Q 50/22* (2013.01); *G16H 15/00* (2018.01); *G16H 50/30* (2018.01)

(58) Field of Classification Search
None
See application file for complete search history.

(56) References Cited

U.S. PATENT DOCUMENTS

| | | | |
|---|---|---|---|
| 2010/0251117 A1* | 9/2010 | Baughman | G16H 50/50 715/706 |
| 2013/0325493 A1* | 12/2013 | Wong | G06F 19/00 705/2 |
| 2014/0074454 A1* | 3/2014 | Brown | G10L 15/08 704/9 |

FOREIGN PATENT DOCUMENTS

| | | | |
|---|---|---|---|
| JP | 2001-526104 A | 12/2001 | |
| JP | 2007-310632 A | 11/2007 | |
| KR | 10-2002-0008934 A | 2/2002 | |

OTHER PUBLICATIONS

International Search Report dated Aug. 11, 2015, issued in counterpart International Application No. PCT/KR2015/003441 (7 pages).

(Continued)

*Primary Examiner* — Michael Tomaszewski
(74) *Attorney, Agent, or Firm* — Westerman, Hattori, Daniels & Adrian, LLP

(57) ABSTRACT

The present invention relates to an apparatus and method for providing a virtual treatment experience which can make a user to understand the necessity for treatment and learn how to counteract side effects of the treatment. The apparatus may include a patient information manager configured to acquire medical information including disease name and blood value of a patient and treatment information including treatment program information and prescription information, a virtual activity provider configured to proceed with a (Continued)

virtual activity according to a manipulation command from a user terminal of the patient and provide an additive score and a subtractive score according to a result of proceeding with the virtual activity, and a controller configured to calculate health value information by quantifying a current health condition of the patient based on the blood value of the patient, select a first display image of an avatar corresponding to the calculated health value information, recalculate the heath value information of the patient using health value information set according to the number of days for which the treatment program has been applied and the provided additive score and subtractive score, and change the first display image of the avatar to a second display image according to the recalculated health value information of the patient.

14 Claims, 14 Drawing Sheets

(51) Int. Cl.
*G16H 15/00* (2018.01)
*G06Q 50/22* (2018.01)
*G06Q 10/10* (2012.01)

(56) References Cited

OTHER PUBLICATIONS

Office Action dated Nov. 5, 2015 for counterpart Korean Patent Application No. 10-2015-0142117 (5 pages).

\* cited by examiner

APPARATUS AND METHOD FOR PROVIDING VIRTUAL TREATMENT EXPERIENCE

TECHNICAL FIELD

The present invention relates to a virtual experience service, and more particularly, to an apparatus and method for providing a virtual treatment experience which can cause a user to understand the necessity for treatment and learn how to counteract side effects of the treatment.

BACKGROUND ART

Even when a medical staff suggests an optimal treatment method for a patient to cure the patient, if the treatment does not proceed according to the plan or the patient cannot stick to the plan, an optimal treatment is not achieved. This is referred to as compliance. Particularly for a chronic disease which requires long-term care, compliance is one of the important factors which determine treatment effects.

In other words, when a patient gives up treatment, even a treatment via an optimal treatment method fails. Particularly, patients who are receiving treatment for cancer necessarily experience nausea, vomiting, etc., and many of the patients refuse or give up treatment due to such side effects and worsen their conditions.

Accordingly, there is a need for a method for raising a patient's compliance and participation level in a treatment program and maximizing the effects of a treatment program.

DISCLOSURE

Technical Problem

The present embodiment is directed to providing an apparatus and method for providing a virtual treatment experience so that drug prescription and treatment are provided for the number of treatment days during a period that is the same as an actual treatment program, thus causing a patient to learn a treatment process in advance, relieve anxiety about the treatment, and learn correct treatment information and solutions to side effects.

The present embodiment is also directed to providing an apparatus and method for providing a virtual treatment experience which can provide an avatar that reflects physical changes made according to the progress of a treatment program and also can quantify and apply a user's compliance with the treatment program to changes in the avatar's body.

The present embodiment is also directed to providing an apparatus and method for providing a virtual treatment experience which can further induce a patient to engage in virtual activities, such as cooking, farming (cultivation of crops), walking, exercising, etc., in a game by applying treatment effects amplified through the virtual activities to the condition of an avatar and displaying the condition of the avatar, and thereby can induce the patient to actually engage in physical activities or cause the patient to acquire self-treatment information.

The present embodiment is also directed to providing an apparatus and method for providing a virtual treatment experience which support chatting with other users in a virtual space of a game so that a user may exchange information and obtain emotional support such as a sense of fellowship, thus relieving the user's anxiety about treatment and providing emotional stability to the user.

Technical Solution

One aspect of the present invention for solving the aforementioned technical problems provides a method of providing a virtual treatment experience, the method including: a first operation of acquiring medical information including disease name and blood value of a patient and treatment information including treatment program information and prescription information; a second operation of calculating health value information by quantifying a current health condition of the patient based on the medical information of the patient, and selecting a display image of an avatar corresponding to the calculated health value information; a third operation of proceeding with a virtual activity according to a manipulation command from a user terminal of the patient, and providing an additive score and a subtractive score according to a result of proceeding with the virtual activity; a fourth operation of calculating a heath value of the patient using health value information set according to the number of days for which the treatment program has been applied and the provided additive score and subtractive score; and a fifth operation of changing the display image of the avatar according to the calculated health value of the patient.

Another aspect of the present invention for solving the aforementioned technical problems provides an apparatus for providing a virtual treatment experience, the apparatus including: a patient information manager configured to acquire medical information including disease name and blood value of a patient and treatment information including treatment program information and prescription information; a virtual activity provider configured to proceed with a virtual activity according to a manipulation command from a user terminal of the patient, and provide an additive score and a subtractive score according to a result of proceeding with the virtual activity; and a controller configured to calculate health value information by quantifying a current health condition of the patient based on the blood value of the patient, select a first display image of an avatar corresponding to the calculated health value information, recalculate the heath value information of the patient using health value information set according to the number of days for which the treatment program has been applied and the provided additive score and subtractive score, and change the first display image of the avatar to a second display image according to the recalculated health value information of the patient.

Advantageous Effects

According to the present invention, a patient is made to undergo virtual treatment experience of a treatment program so that the patient's anxiety about the treatment program can be relieved and the patient's understanding of a treatment process can be increased. Therefore, it is possible to amplify treatment effects and also cause the patient to naturally accept changes in his or her body made by side effects of the treatment process.

Also, according to the present invention, a patient looking at an improved appearance of an avatar of a virtual treatment experience service may acquire a positive attitude together with emotional stability that he or she can be cured so.

Therefore, it is possible to raise compliance of the patient and induce the patient to take a positive attitude toward treatment for the patient.

Also, according to the present invention, virtual activities corresponding to activities which are helpful for treatment are provided, and resultant positive effects are applied to and displayed in an avatar. Therefore, positive effects produced by the corresponding activity can be recognized, and it is possible to naturally induce a positive attitude toward a self-treatment process.

Also, according to the present invention, when experience data of a virtual treatment experience service and medical data of hospitals are accumulated, it is possible to estimate the condition of a user by analyzing the experience data of the user, and thus understanding a condition of a patient can be helped.

Also, according to the present invention, a community of people suffering from the same disease can share information and thus can help finding a positive direction for treatments leading to life enhancement.

DESCRIPTION OF DRAWINGS

FIG. 3 is a diagram showing an example of a current condition display screen provided according to an exemplary embodiment of the present invention when a user logs in;

BEST MODE OF THE INVENTION

Figure 1:
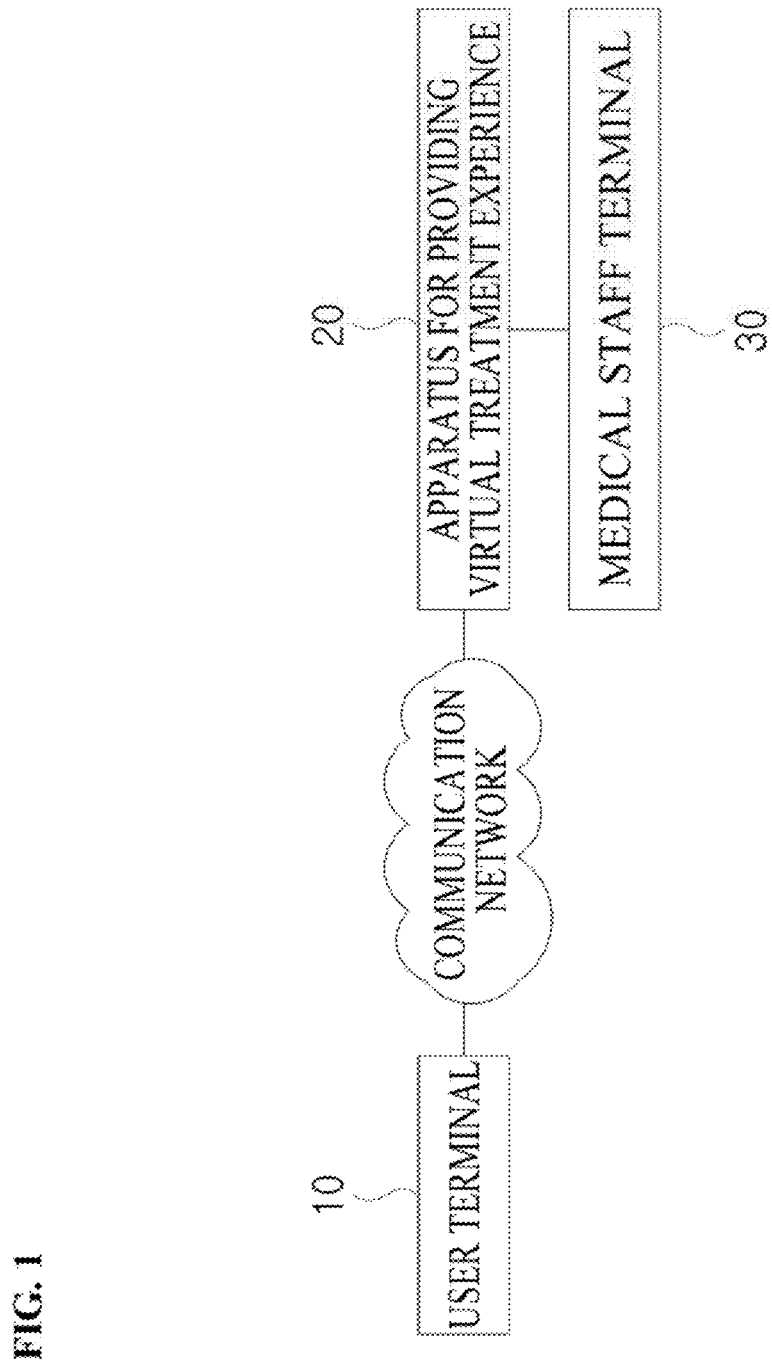
FIG. 1 is a diagram showing an overall network connection of an apparatus for providing a virtual treatment experience according to an exemplary embodiment of the present invention.

One exemplary embodiment of the present invention for solving the aforementioned technical problems may include a method of providing a virtual treatment experience, the method including: a first operation of acquiring medical information including disease name and blood value of a patient and treatment information including treatment program information and prescription information; a second operation of calculating health value information by quantifying a current health condition of the patient based on the medical information of the patient, and selecting a display image of an avatar corresponding to the calculated health value information; a third operation of proceeding with a virtual activity according to a manipulation command from a user terminal of the patient, and providing an additive score and a subtractive score according to a result of proceeding with the virtual activity; a fourth operation of calculating a heath value of the patient using health value information set according to the number of days for which the treatment program has been applied and the provided additive score and subtractive score; and a fifth operation of changing the display image of the avatar according to the calculated health value of the patient.

[Modes Of The Invention]

The above objects, features, and advantages of the present invention will be more apparent from the following detailed description taken in conjunction with the accompanying drawings. However, the present invention may be modified in various ways and have many exemplary embodiments. Therefore, particular embodiments will be shown in the drawings and described in detail below.

In the description of the present invention, the terms "user" and "patient" are used together, but the terms have the same meaning.

FIG. 1 is a diagram showing an overall network connection of an apparatus for providing a virtual treatment experience according to an exemplary embodiment of the present invention.

Referring to FIG. 1, an apparatus 20 for providing a virtual treatment experience according to the present invention may be connected to a plurality of user terminals 10 through a communication network.

Also, the apparatus 20 for providing a virtual treatment experience according to the present invention may be connected to at least one medical staff terminal 30. Here, the medical staff terminal 30 may be connected to the apparatus 20 for providing a virtual treatment experience directly or through the communication network.

The user terminals 10 may be terminals having displays (not shown) which display information processed by the apparatus 20 for providing a virtual treatment experience. The displays may output various provision screens related to a virtual treatment experience service, for example, may display a user interface (UI) or a graphic user interface (GUI) related to the apparatus 20 for providing a virtual treatment experience.

Such user terminals 10 may be implemented as electronic devices in various forms, that is, may be implemented in at least one electronic device among a personal computer (PC), a tablet, a smart phone, a mobile phone, a notebook, and a television (TV), for example.

The medical staff terminal 30 is a terminal for a medical staff in a hospital to access the apparatus 20 for providing a virtual treatment experience and input medical information and treatment information of patients and may be implemented in at least one electronic device among a PC, a tablet, a smart phone, a mobile phone, and a notebook.

The apparatus 20 for providing a virtual treatment experience according to the present invention may provide a virtual treatment experience service to which an actual treatment program for a user has been applied based on treatment information of the user. Here, the treatment information may at least include treatment program information and prescription information.

To this end, the apparatus 20 for providing a virtual treatment experience may operate in conjunction with the medical staff terminal 30 and receive or acquire treatment information of a patient.

In other words, the apparatus 20 for providing a virtual treatment experience may be implemented to provide a virtual treatment experience service for receiving medical information of a patient including the patient's name, sex, disease name, blood value, status, etc. and treatment information of the patient including treatment program information and prescription information from the medical staff terminal 30, generating an avatar reflecting a current health condition of the user based on the received medical information of the patient, and changing the generated avatar by applying, to the avatar, a health condition (a condition in which symptoms have been improved or worsened) according to the number of days for which the treatment program has been applied.

Here, the apparatus 20 for providing a virtual treatment experience may calculate health value information by quantifying a current health condition of the patient using blood value information of the patient and generate a corresponding avatar display image using the calculated health value information. The blood value may vary in type according to the type of a disease. For example, in the case of an anticancer treatment, white blood cell, absolute neutrophil, hemoglobin, platelet, aspartate aminotransferase/alanine aminotransferase (AST/ALT) values, etc. may be used as main indicators.

To this end, the apparatus 20 for providing a virtual treatment experience may set health values in advance according to the number of elapsed days in the treatment period of the treatment program, generate, in advance, display images of the avatar to which physical side effects produced by the progress of the treatment program are applied in stages, and set and store the generated display images of the avatar differently according to ranges of the health values.

Also, the apparatus 20 for providing a virtual treatment experience may be implemented to configure a virtual village including a health club, houses, vegetable gardens, a park, stores, a hospital, a pharmacy, etc., display an avatar of a user in the virtual village, and then support virtual activities of the avatar in the virtual village according to manipulation commands from a user terminal 10.

For example, the apparatus 20 for providing a virtual treatment experience may be implemented to support virtual activities, such as walking in the park, exercising in the health club, cultivation of crops in a vegetable garden, and so on. The apparatus 20 for providing a virtual treatment experience may provide an additive score and a subtractive score according to the participation level in such virtual activities to apply the additive score and the subtractive score to a health condition, so that the additive score and the subtractive score may be applied to a change in the condition of the avatar.

In other words, when basic physical changes have been set according to a treatment period of a treatment program, the apparatus 20 for providing a virtual treatment experience may be implemented to slow or accelerate the set basic physical changes by making additive physical changes due to an additive score and a subtractive score obtained through virtual activities. In this way, the apparatus 20 for providing a virtual treatment experience may lead virtual activities of a patient in a direction in which physical changes of the avatar are slowed, that is, in a direction in which a positive change can be made.

Further, the apparatus 20 for providing a virtual treatment experience may cause a plurality of user terminals connected through the communication network to operate in conjunction with one another. The apparatus 20 for providing a virtual treatment experience may be implemented to display avatars of other connected user terminals and non player characters (NPCs) residing in the village, all in a virtual village and support community activities, such as greeting conversations, etc. with the avatars of other users and the NPCs residing in the village.

For example, the apparatus 20 for providing a virtual treatment experience may make it possible to exchange information and obtain emotional support through interaction with avatars of other users based on message transmission and chatting functions.

As described above, an apparatus for providing a virtual treatment experience according to the present invention may display an avatar to reflect physical changes made in a treatment period of a treatment program of a patient and display a display image of the avatar changed by additionally applying virtual activity information. In this way, the present invention can provide a patient with indirect experience of a treatment process, thus facilitating understanding of a necessity for treatment and a treatment process and causing the patient to naturally accept changes in his or her body and side effects produced by the treatment process. Also, when the patient performs an activity helpful for treatment, the present invention makes a positive change in a display image of the avatar, thus promoting a positive attitude toward treatment.

Figure 2:
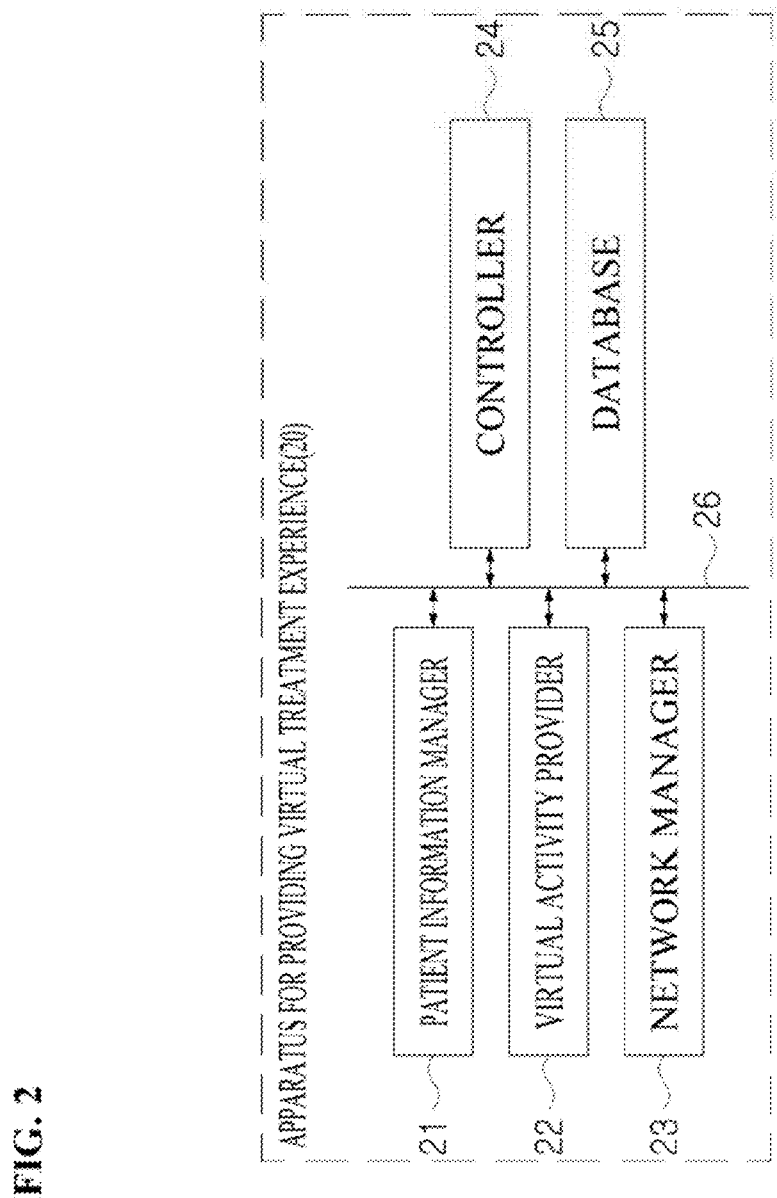
FIG. 2 is a diagram showing an example of a detailed configuration of the apparatus for providing a virtual treatment experience shown in FIG. 1.

FIG. 2 is a diagram showing an example of a detailed configuration of the apparatus for providing a virtual treatment experience shown in FIG. 1.

Referring to FIG. 2, the apparatus 20 for providing a virtual treatment experience according to the present invention may include a patient information manager 21, a virtual activity provider 22, a network manager 23, a controller 24, and a database 25.

The patient information manager 21 processes membership registration of users and stores membership subscription information (e.g., basic personal information including names, ages, birthdates, etc.) and may store and manage identifiers (IDs) and passwords of members for each of the members.

Also, the patient information manager 21 may integrate medical information of patients input from the medical staff terminal 30 with the membership subscription information and manage the medical information and the membership subscription information. Here, the medical information of patients may include name, sex, age, disease name, blood examination result information (blood value information), status information, etc. of the patients.

Further, the patient information manager 21 may acquire and store treatment program information, prescription information, precaution information, etc. of patients, input from the medical staff terminal 30.

The virtual activity provider 22 may proceed with a virtual activity according to a manipulation command from a user terminal 10 of a patient and provide an additive score and a subtractive score according to a result of proceeding with the virtual activity. Here, the virtual activity may be one of drug taking, cooking, walking, crop cultivation, exercising, shopping, and a community activity.

In other words, the virtual activity provider 22 may be implemented to configure a virtual village including a health club, houses, vegetable gardens, a park, stores, a hospital, a pharmacy, etc., display an avatar of a user in the virtual village, and then support a virtual activity (e.g., cooking healing food, going for a walk, exercising in a health club, etc.) of the avatar in the virtual village according to a manipulation command from a user terminal 10. Here, the virtual activity provider 22 may be implemented to provide an additive score and a subtractive score, which are applied to a health value, with weights differing according to virtual activities.

Here, the virtual activity provider 22 may be implemented to provide help with self-treatment of each user, such as information of how virtual activities help with a health condition of an avatar, how the avatar's health can be improved more effectively, etc., when virtual activities including cooking, walking, exercising, etc. are performed using the avatar.

For example, when the avatar purchases cooking materials at a store, the virtual activity provider 22 may distinguish between cooking materials to be avoided and other cooking materials using medical information of the user and provide recommended cooking materials and recipes for the cooking materials. Here, the virtual activity provider 22 may be implemented to provide help on how and which ingredients help according to each cooking material.

In another example, when providing a virtual activity such as crop cultivation, the virtual activity provider 22 causes a user to select a crop to be grown and may be implemented to provide help on how the crop helps with a treatment and a health condition of the user together. The virtual activity provider 22 may be implemented to display a growth process of a crop to be grown in a vegetable garden when the crop is selected.

Also, the virtual activity provider 22 may be configured to provide an additive score to be applied to a health value when a user prepares a healthful meal using cooking materials helpful for treatment and health and eats the meal. Conversely, the virtual activity provider 22 may be configured to provide a subtractive score to be applied to a health value when a user has harmful food which is unhelpful for treatment.

In still another example, when providing virtual activities including walking, exercising, etc., the virtual activity provider 22 may be configured to provide help by recommending amounts of walking and exercising, types of exercise, etc. suited to the current condition of an avatar. The virtual activity provider 22 may be implemented to provide an additive score to be applied to a health value when a user performs virtual activities helpful for treatment, such as walking and exercising.

In yet another example, the virtual activity provider 22 provides information on treatment programs related to treatment for all diseases and may be implemented to automatically prescribe drugs to be taken during the corresponding treatment period according to a selection of a treatment program. Here, the treatment programs and the prescribed drugs are identical to those of actual treatment programs and prescribed drugs, and the prescribed drugs according to the treatment program are designed to be taken at a time designated by a hospital within a period designated by the same. The virtual activity provider 22 may also provide an alarm function for taking a drug at an appropriate time, so that a user may be induced to take a drug at an accurate time.

When a user does not take prescribed drug at the right time, the virtual activity provider 22 may apply a resultant subtractive score to a health value, and cause a resultant health value to be applied to an expression of an avatar and a change in the physical condition.

Further, the virtual activity provider 22 may generate NPCs residing in a virtual village and configure the NPCs to exchange greetings with an avatar of a user or provide information helpful for treatment. Here, the NPCs residing in the virtual village may be neighbors, store clerks, men and women of police, hospital staff members, pharmacy clerks, and so on.

The virtual activity provider 22 may be configured to perform a friend-inviting function, a friend-adding function, a message transmission function, a gift-sending function, etc. when the avatar of the user performs a communication activity. In this way, the user may exchange information with other users who suffer from a disease identical or similar to the disease of the user and form mental bonds with the other users.

The network manager 23 may communicate with an external terminal through the communication network.

The controller 24 may control the virtual activity provider 22 to proceed with a virtual treatment experience and virtual activities according to programmed virtual treatment experience scenarios, generate the results as a GUI screen, and provide the GUI screen.

Also, the controller 24 may calculate health value information by quantifying a current health condition of a patient based on a blood value included in medical information of the patient and select and provide a display image of an avatar corresponding to the calculated health value information.

At this time, the controller 24 may generate a GUI screen including at least an avatar display image of the user, a current health value, and the number of days for which a treatment program has been applied and then provide the GUI screen to a user terminal 10. For example, when the user is in an anticancer treatment, health values may use values representing white blood cell, absolute neutrophil, hemoglobin, platelet, and AST/ALT values in percentages, which are main indicators in an anticancer treatment. Here, the health values may be one of the factors that cause a change of appearance of the avatar in addition to the number of days for which the treatment program has been applied.

As described above, the controller 24 may provide a basic display image of an avatar to a user who has gained membership. Subsequently, the controller 24 may provide an avatar editing tool for dressing an avatar up with accessories, clothes, etc., but does not allow changing the basic display image.

Further, the controller 24 may change a display image of an avatar by applying a physical change made over a treatment period of a treatment program to a basic display image of the avatar. For example, the controller 24 may change an expression and a physical condition of the avatar so that side effects produced over the treatment period of the treatment program may be shown in the expression and the physical condition of the avatar.

In other words, when a user is in an anticancer treatment, the controller 24 may implement a change in an expression of an avatar according to a blood health value and physical side effects produced by the anticancer treatment to be directly applied and shown in the expression and a physical condition of the avatar.

Moreover, the controller 24 may recalculate heath value information of the patient using health value information set according to the number of days for which a treatment program has been applied and a provided additive score and subtractive score and change a basic display image of an avatar to another display image according to the recalculated health value information of the patient.

In other words, the controller 24 may display different display conditions of the avatar according to changes in the health value of the avatar of the user. Here, the health value of the avatar may vary according to the progress of a virtual treatment experience scenario. For example, the health value of the avatar may be increased or reduced due to a lapse of a period of the treatment program, acquisition of an additive score and a subtractive score through virtual activities, and so on.

In this way, a user may check his or her health condition through how his or her avatar appears and boost his or her will to improve his or her health condition.

The database 25 may store various kinds of information related to the virtual treatment experience service. For example, the database 25 may classify and store membership subscription information, medical information, treatment information, virtual activity information, health value information, etc. of users for each of the users.

As described above, a user can examine a change in his or her health condition through a virtual treatment experience according to the present invention. The user can obtain vicarious satisfaction when a health condition is good and can boost his or her will to improve the health condition of an avatar when the health condition worsens.

Also, when a treatment period of a treatment program elapses, a user can estimate a change in his or her condition and naturally acquire self-treatment information through a virtual treatment experience according to the present invention by looking at the appearance of an avatar to which changes in a health value according to side effects and virtual activities have been applied.

An example case of applying a virtual treatment experience service according to an exemplary embodiment of the present invention to an anticancer treatment service will be described below. However, the present invention is not limited to the anticancer treatment service, and it is self-evident that the present invention can be applied to treatment for other diseases.

Figure 3:
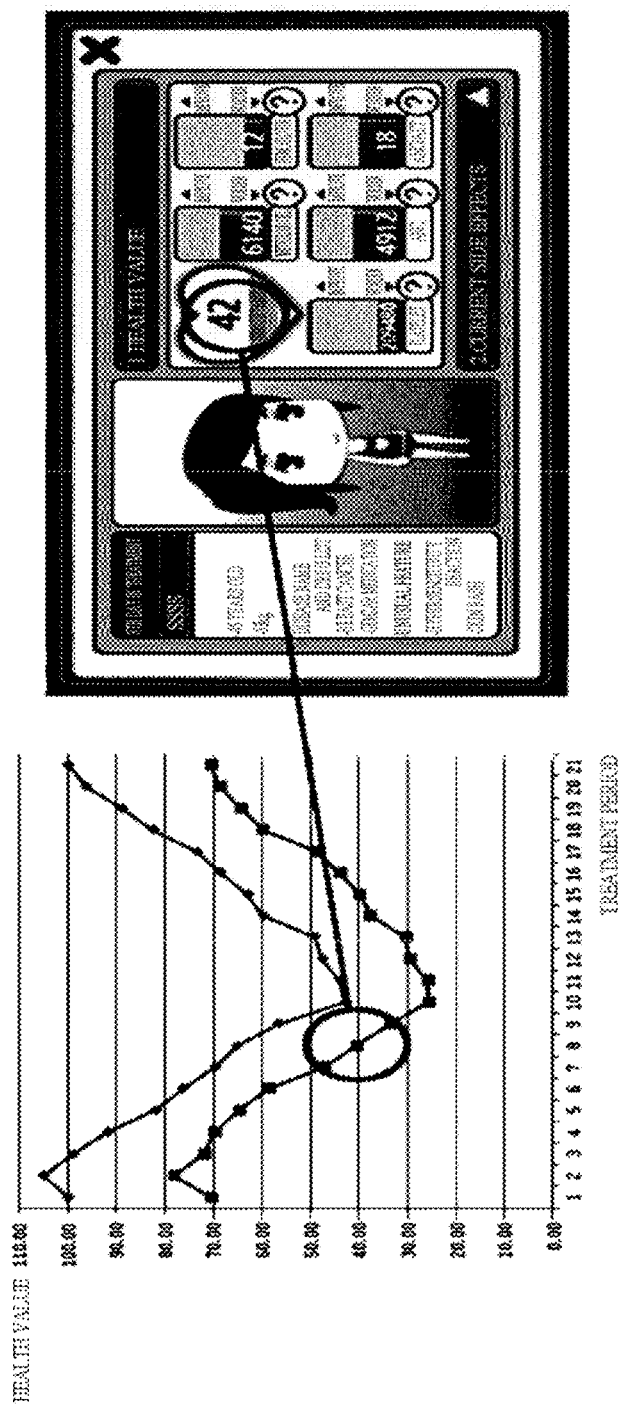

FIG. 3 is a diagram showing an example of a current condition display screen provided according to an exemplary embodiment of the present invention when a user logs in. (a) is an example of a graph showing changes in a health value according to treatment program periods, and (b) is an example of a current condition display screen of an avatar.

Referring to (a) of FIG. 3, in the present embodiment, a basic health value may be set in advance according to the number of days for which a treatment program has been applied. As a treatment period elapses, different appearances of an avatar may be displayed using the preset basic health value.

For example, when the number of days for which a treatment program has been applied is eight, a health value becomes 42 and may be displayed in an area for displaying a health condition in a current condition display screen of an avatar as shown in (b) of FIG. 3.

Referring to (b) of FIG. 3, a current condition display screen of an avatar according to the present embodiment may include an area for displaying the number of days for which a treatment program has been applied, an area for displaying basic information of a user, an area for displaying an avatar of the user, an area for displaying a health condition of the user, and so on.

The area for displaying basic information of a user may include name, age, disease name, name of a drug in use, unusual features, and so on.

The area for displaying an avatar may be configured to display only the face of an avatar or the whole body. When the whole body is displayed, the area for displaying an avatar may be implemented to reflect a change in the weight.

The area for displaying a health condition may include a health value obtained by quantifying a current health condition of an avatar and a blood examination value. For example, the health value may be calculated by converting white blood cell, absolute neutrophil, hemoglobin, platelet, and AST/ALT values into percentages, which are main indicators in an anticancer treatment. The blood examination value may be values of white blood cells, absolute neutrophils, hemoglobin, platelets, and AST/ALT in blood.

Figure 4:
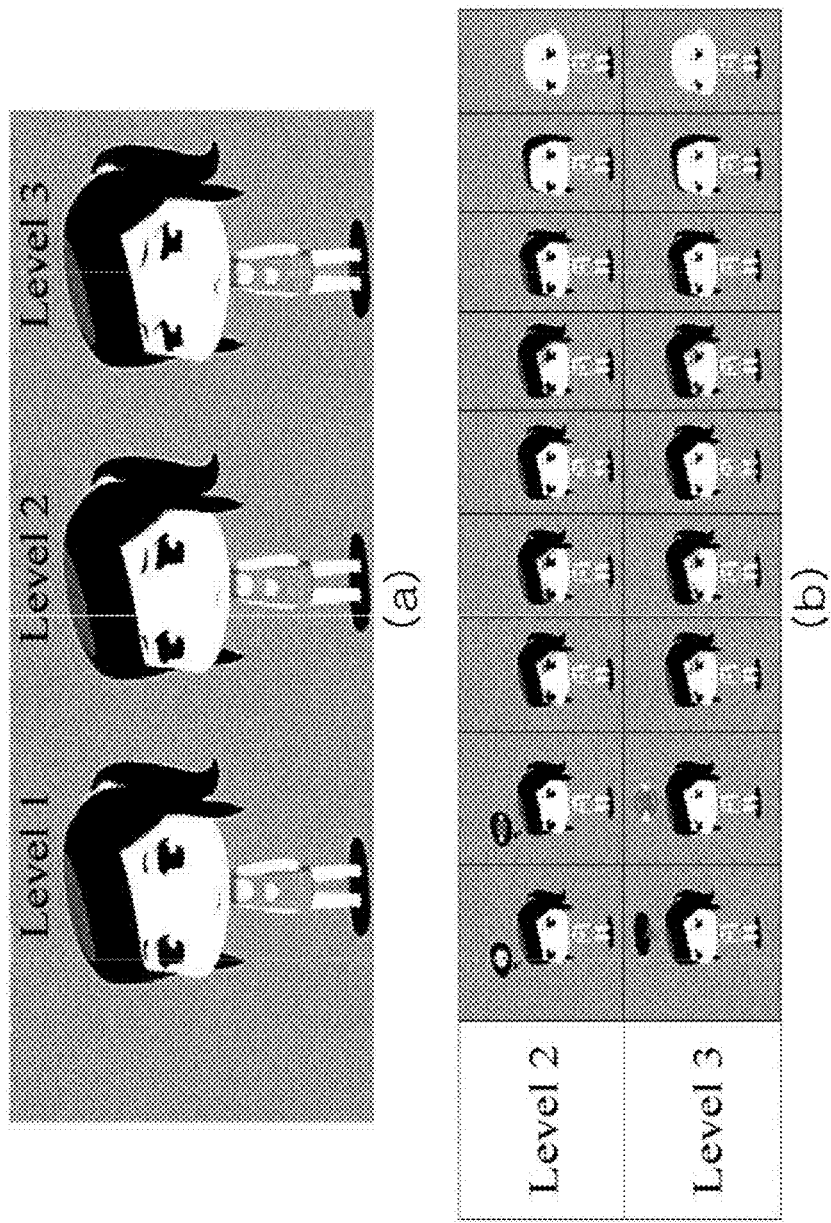
FIG. 4 is a diagram showing examples of display conditions of an avatar according to an exemplary embodiment of the present invention.

FIG. 4 is a diagram showing examples of display conditions of an avatar according to an exemplary embodiment of the present invention. (a) shows a case in which display conditions of an avatar are largely classified into three stages, and (b) shows a case in which display conditions of the avatar are subdivided according to each stage shown as an example in (a).

Referring to (a) and (b) of FIG. 4, display conditions of an avatar may be largely classified into level 1, level 2, and level 3, and each level may be classified into sub-stages including whole body muscle pain, anorexia, neutrophil intermittent fever, itching and a skin rash, hand-foot syndrome, vomiting (nausea and stomatitis), alopecia 1, alopecia 2, alopecia 3, and so on.

Such display conditions of an avatar reflects side effects produced with the progress of a treatment program.

Figure 5:
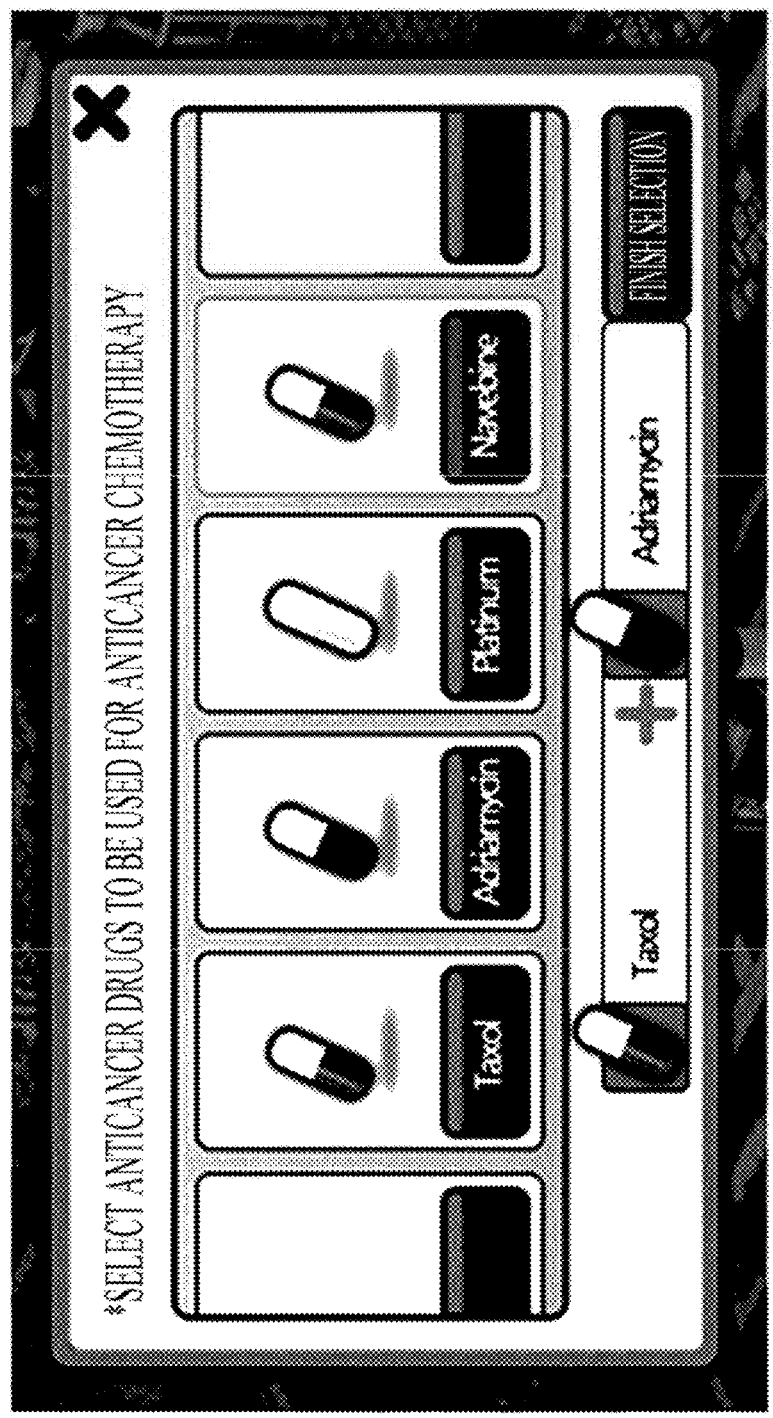
FIG. 5 is a diagram showing an example of a prescription information generation screen according to an exemplary embodiment of the present invention.

FIG. 5 is a diagram showing an example of a prescription information generation screen according to an exemplary embodiment of the present invention.

Referring to FIG. 5, the apparatus 20 for providing a virtual treatment experience may provide a GUI screen which is implemented to display and select anticancer drugs to be used for an anticancer chemotherapy. To this end, the apparatus 20 for providing a virtual treatment experience collects and stores all treatment program information of various anticancer chemotherapies.

In other words, a medical staff of a hospital may access the apparatus 20 for providing a virtual treatment experience through the medical staff terminal 30 and input treatment program information and prescription information of a patient.

At this time, although not shown in the drawing, the apparatus 20 for providing a virtual treatment experience may provide a GUI screen for inputting patient information and then provide a GUI screen for selecting drugs to be used in the corresponding treatment program as shown in FIG. 5 so that treatment program information can be input.

Figure 6:
FIG. 6 is a diagram showing an example of prescription information according to an exemplary embodiment of the present invention.

FIG. 6 is a diagram showing an example of prescription information according to an exemplary embodiment of the present invention.

As shown in FIG. 6, the apparatus 20 for providing a virtual treatment experience according to the present invention may provide a GUI screen displaying prescription information of a user when the user generates an avatar. Here, the prescription information may be input from the medical staff terminal and stored in advance and provided through an inquiry and search using login information of the user or acquired after requested through the medical staff terminal.

The GUI screen displaying the prescription information may be implemented to display names of prescribed drugs, symptoms corresponding to the drugs, the number of days available for taking the drugs, and confirmation of whether or not the corresponding drugs have been received. For example, when a "Receive" icon is clicked, the corresponding drug is received and displayed in "My drug box" (not shown), and the "Receive" icon may be changed to a "Finish receipt" icon. Here, the prescribed drugs may be identical to drugs taken in an actual treatment program.

Figure 7:
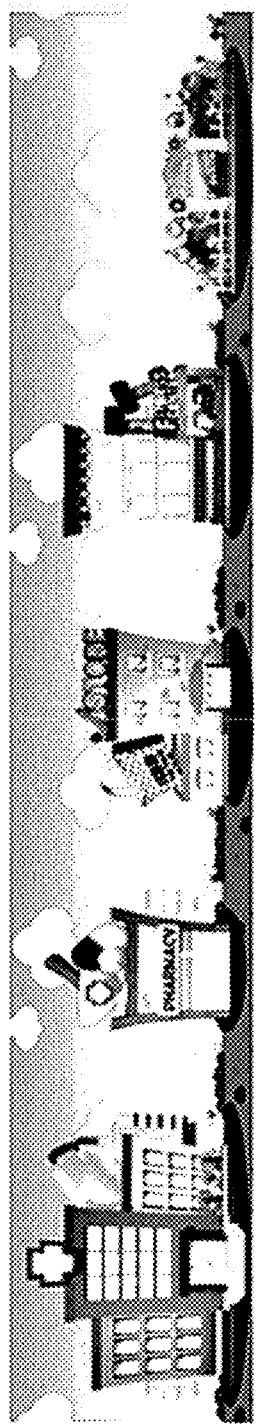
FIG. 7 is a diagram showing an example of a virtual village according to an exemplary embodiment of the present invention.

FIG. 7 is a diagram showing an example of a virtual village according to an exemplary embodiment of the present invention.

As shown in FIG. 7, in the present embodiment, a virtual environment in which an avatar performs actions may be implemented in the form of a virtual village, and a GUI screen may be provided, in which a virtual village is configured to include a hospital, a pharmacy, stores, a health club, a park, and so on.

Through the GUI screen, a user may perform a virtual activity of purchasing cooking materials at a store, walking in the park, exercising in the health club, etc. using an avatar.

For example, when the avatar is moving in front of each building, an "Enter" icon may be generated to allow entrance, or when the avatar moves toward the inside of a building using a movement key, the avatar may automatically enter the building, and accordingly, a GUI screen in which the avatar has moved to the inside of the building may be provided.

Figure 8:
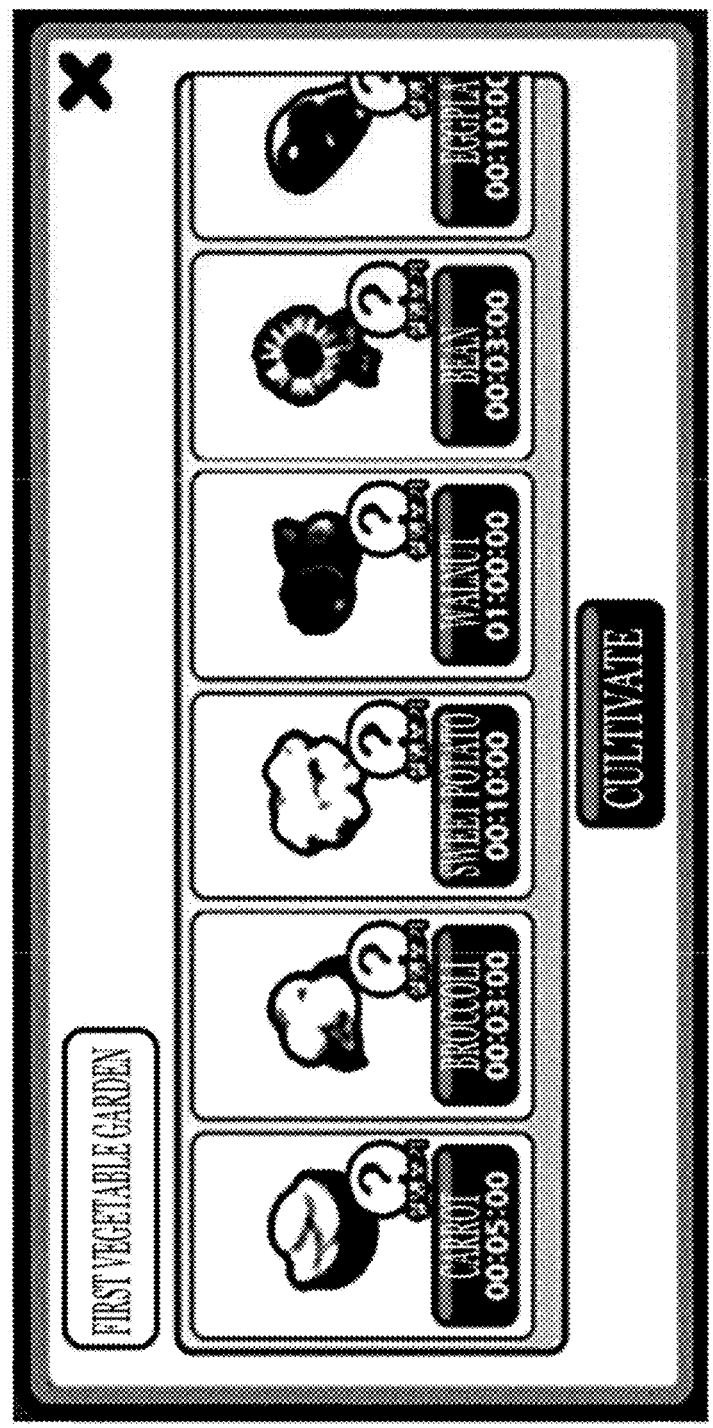
FIG. 8 is a diagram showing an example of cultivation of crops among virtual activities according to an exemplary embodiment of the present invention.

FIG. 8 is a diagram showing an example of crop cultivation among virtual activities according to an exemplary embodiment of the present invention.

As shown in FIG. 8, in the present embodiment, a GUI screen for selecting a crop to be grown in a vegetable garden may be provided, and images and names of crops, time to grow the crop, "Detailed description" icons, etc. may be included in the GUI screen. When a "Detailed description" icon is selected, help on the characteristics of the corresponding crop and how the crop helps in relation to a disease of a user may be displayed.

In such a GUI screen, crop images may be provided in the form of thumbnail images, and when a particular crop is selected and then a "Cultivate" icon is selected, a process in which the selected particular crop is planted in a vegetable garden and grown may be shown. Subsequently, when cultivation of the crop is completed, a notification may be provided, and it is possible to harvest the crop using a "Harvest (Gather)" icon. The crop harvested in this way may be registered and managed as a retained crop, and may be reduced when used in cooking, for gift presenting, and so on.

Figure 9:
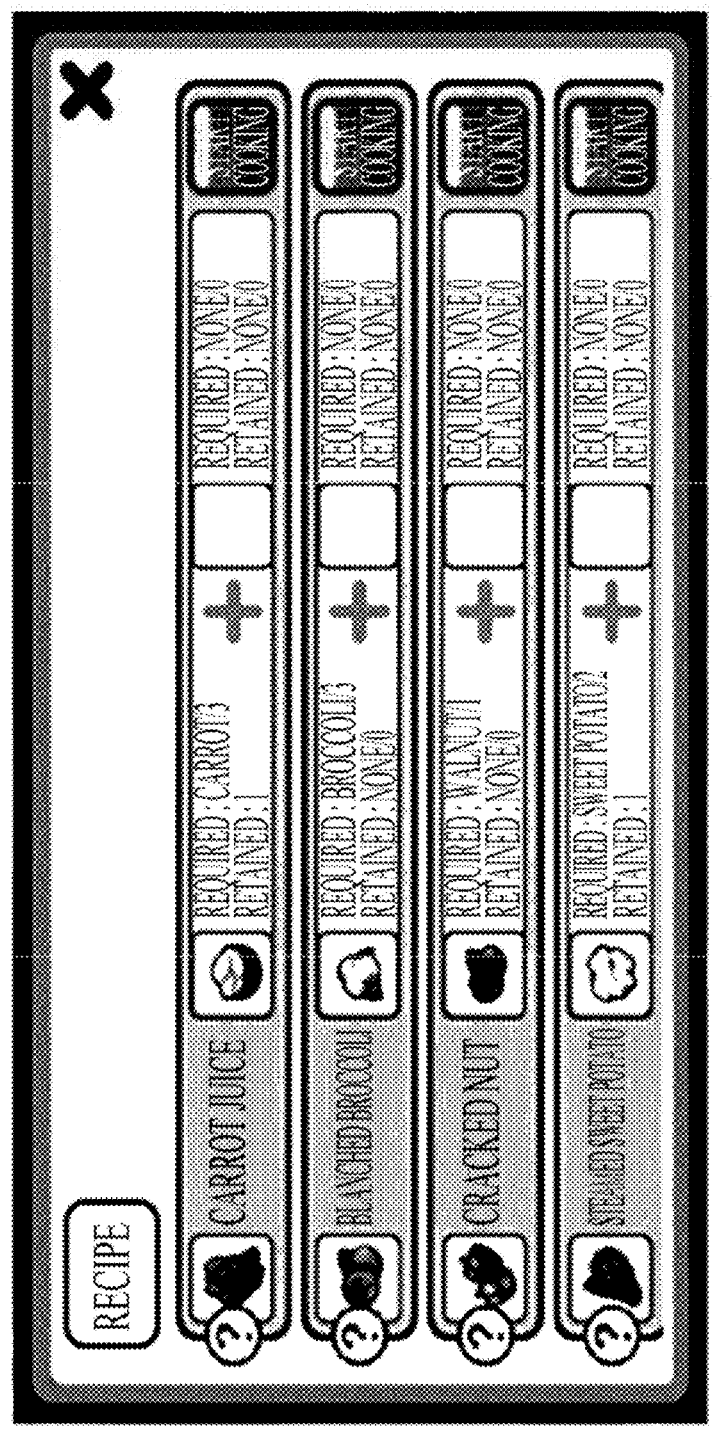
FIG. 9 is a diagram showing an example of cooking among virtual activities according to an exemplary embodiment of the present invention.

FIG. 9 is a diagram showing an example of cooking among virtual activities according to an exemplary embodiment of the present invention.

As shown in FIG. 9, in the present embodiment, a GUI screen for selecting food to be cooked may be provided, and food names, required ingredients, retained ingredients, a "Start cooking" icon, etc. may be included in the GUI screen. An icon for providing help on how the corresponding food helps with treatment of a user when the user eats the food and a "Recipe" icon may be further included.

Figure 10:
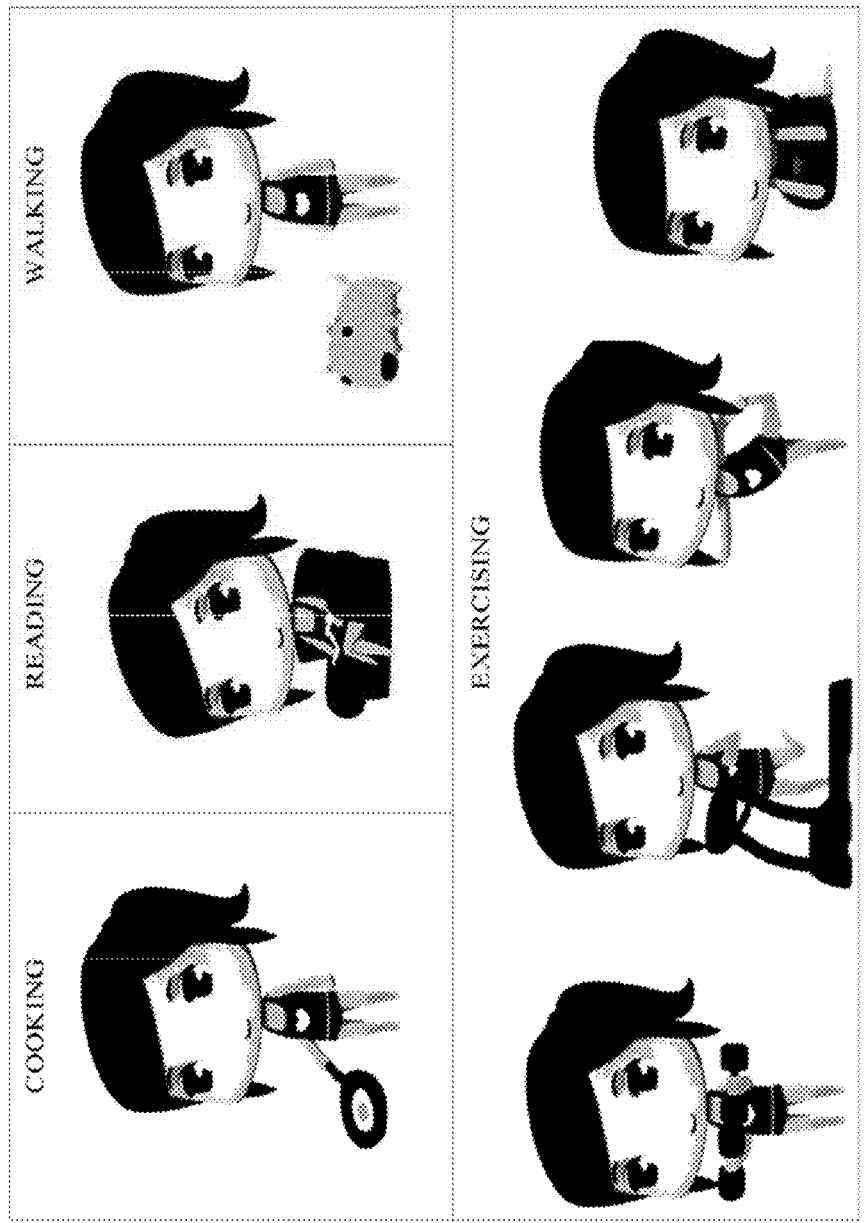
FIG. 10 is a diagram showing example appearances of an avatar during virtual activities according to an exemplary embodiment of the present invention.

FIG. 10 is a diagram showing example appearances of an avatar during virtual activities according to an exemplary embodiment of the present invention.

As shown in FIG. 10, the present invention may be implemented so that, when a user performs virtual activities including cooking, reading, walking, exercising, etc. using his or her avatar, appearances corresponding to the virtual activities may be applied to the avatar.

For example, an appearance of the avatar may be displayed corresponding to preparing food with a kitchen tool required for the food in the case of cooking, reading a book in the case of reading, exercising and his or her body using exercise equipment in the case of exercising, and so on.

Figure 11:
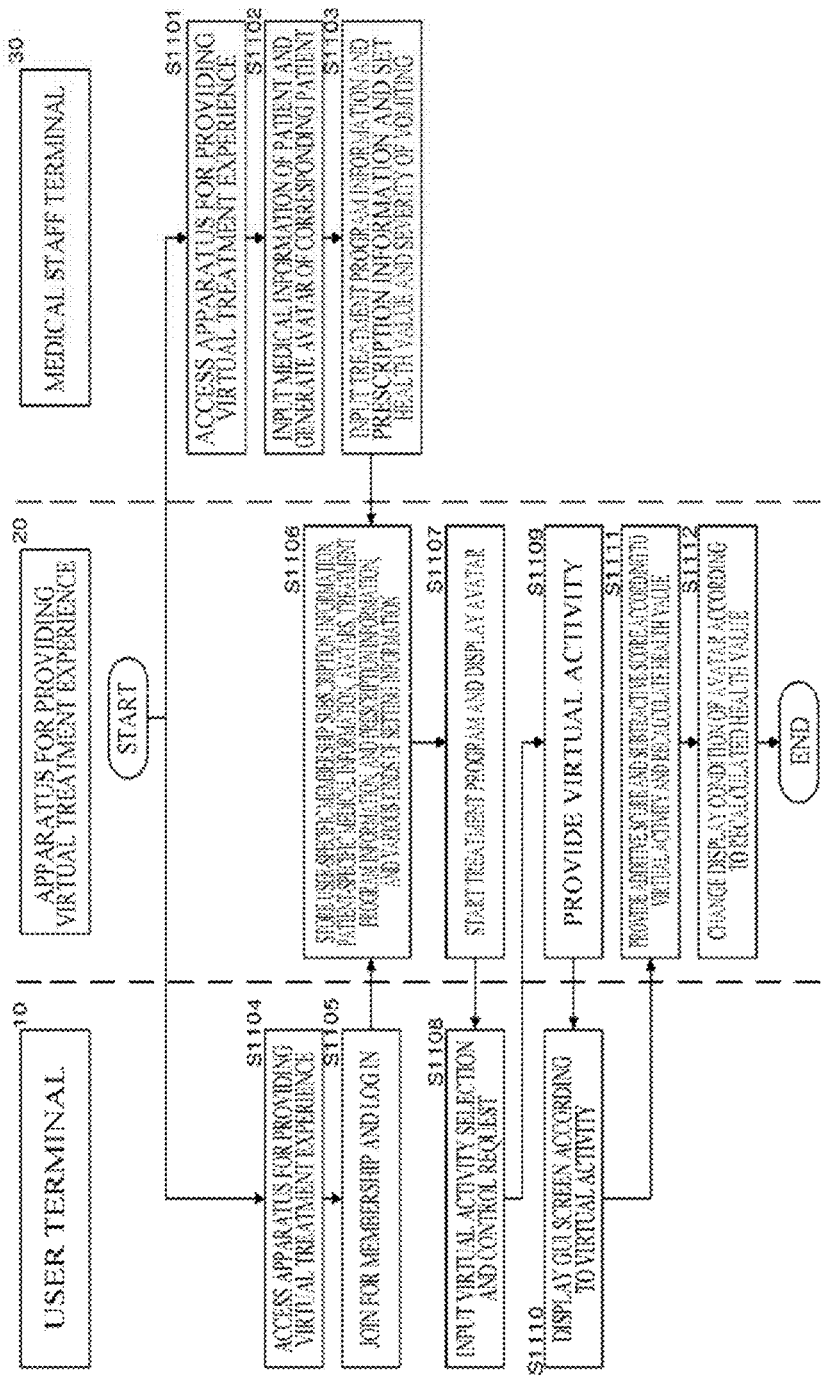
FIG. 11 is a diagram showing an example of a method of providing a virtual treatment experience according to an exemplary embodiment of the present invention.

FIG. 11 is a diagram showing an example of a method of providing a virtual treatment experience according to an exemplary embodiment of the present invention.

Referring to FIG. 11, in a method of providing a virtual treatment experience according to the present invention, a medical staff of a hospital may access the apparatus 20 for providing a virtual treatment experience through the medical staff terminal 30 first (S1101), and then generate an avatar of a patient after inputting medical information of the patient (S1102).

Here, when the medical staff terminal 30 accesses the apparatus 20 for providing a virtual treatment experience, the apparatus 20 for providing a virtual treatment experience may carry out a login procedure for the corresponding medical staff. In the case of a nonmember, the apparatus 20 for providing a virtual treatment experience may induce the medical staff to obtain membership subscription and proceed with subsequent membership joining procedure. Also, the apparatus 20 for providing a virtual treatment experience may separately provide a GUI screen for inputting medical information of a patient and a GUI screen for generating an avatar. At this time, the medical staff terminal 30 displays a provided GUI screen, and it is possible to input medical information of the patient or generate an avatar according to the displayed GUI screen.

Subsequently, the medical staff may input treatment program information and prescription information of the patient through the medical staff terminal 30 and set a current condition of the patient by setting a health value and the severity of vomiting (S1103).

A plurality of user terminals 10 may access the apparatus 20 for providing a virtual treatment experience (S1104), and the apparatus 20 for providing a virtual treatment experience may proceed with membership joining and login procedures between the plurality of user terminals 10 and the apparatus 20 for providing a virtual treatment experience (S1105).

Then, the apparatus 20 for providing a virtual treatment experience may store and manage membership subscription information of users, patient-specific medical information input by a medical staff, avatar generation information, treatment program information, prescription information, and various kinds of setting information (S1106). Here, using membership subscription information of a user, the apparatus 20 for providing a virtual treatment experience may inquire about medical information of the corresponding patient. When there is medical information of the corresponding patient, the apparatus 20 for providing a virtual treatment experience may inquire about an avatar, treatment program information, prescription information, etc. of the patient.

After that, the apparatus 20 for providing a virtual treatment experience may start a treatment program of the patient corresponding to the user and display the set avatar of the user (S1107). Here, the displayed avatar may have been set by a medical staff to show the current condition of the user.

Subsequently, when virtual activity selection information and a control request for the corresponding virtual activity are input from a user terminal 10 (S1108), the apparatus 20 for providing a virtual treatment experience may provide the virtual activity according to the virtual activity selection information (S1109), and the user terminal 10 may display a GUI screen according to the provided virtual activity (S1110).

Then, the apparatus 20 for providing a virtual treatment experience may provide an additive score and a subtractive score according to the virtual activity and then recalculate the set health value by applying the provided additive score and subtractive score (S1111).

After that, the apparatus 20 for providing a virtual treatment experience may change a display condition of the avatar according to the recalculated health value and display the changed display condition (S1112).

In other words, according to the present invention, when a user performs a virtual activity helpful for treatment, an additive score is provided to make a positive change in a displayed shape of an avatar, so that the patient can be naturally induced to take an active posture toward treatment. Conversely, when a user performs a virtual activity unhelpful for treatment, a subtractive score is provided to make a negative change in a displayed shape of an avatar, so that the patient can become aware of importance of compliance with a treatment program and be induced to go through a correct treatment process.

Figure 12:
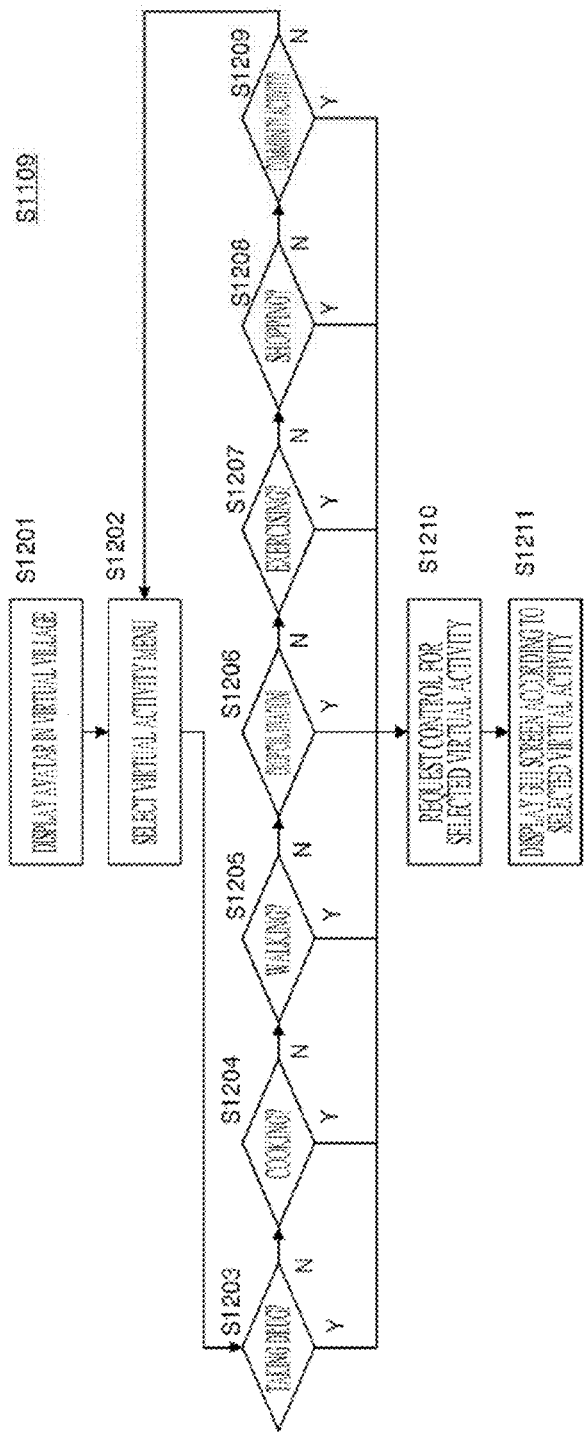
FIG. 12 is a diagram showing an example of a detailed configuration of a process of inputting a virtual activity selection and a control request shown in FIG. 11.

FIG. 12 is a diagram showing an example of a detailed configuration of a process of inputting a virtual activity selection and a control request shown in FIG. 11.

Referring to FIG. 12, in the process of inputting a virtual activity selection and a control request (S1109), a GUI screen showing the avatar in a virtual village provided by the apparatus 20 for providing a virtual treatment experience may be displayed (S1201).

Subsequently, the user may select a virtual activity menu (S1202 to S1209) and request control over the selected virtual activity (S1210). Here, the virtual activity may be at least one of taking a drug, cooking, walking, crop cultivation, exercising, shopping, and a community activity.

Then, a GUI screen according to the selected virtual activity may be received from the apparatus 20 for providing a virtual treatment experience and displayed (S1211). Here, the GUI screen according to the virtual activity may show, for example, a drug to be taken when the selected virtual activity is taking a drug, and may show, in another example, an avatar that performs the corresponding activity as shown in FIG. 10, when the selected virtual activity is cooking. In other words, the GUI screen according to the virtual activity may show an appearance of the avatar performing the virtual activity.

Figure 13:
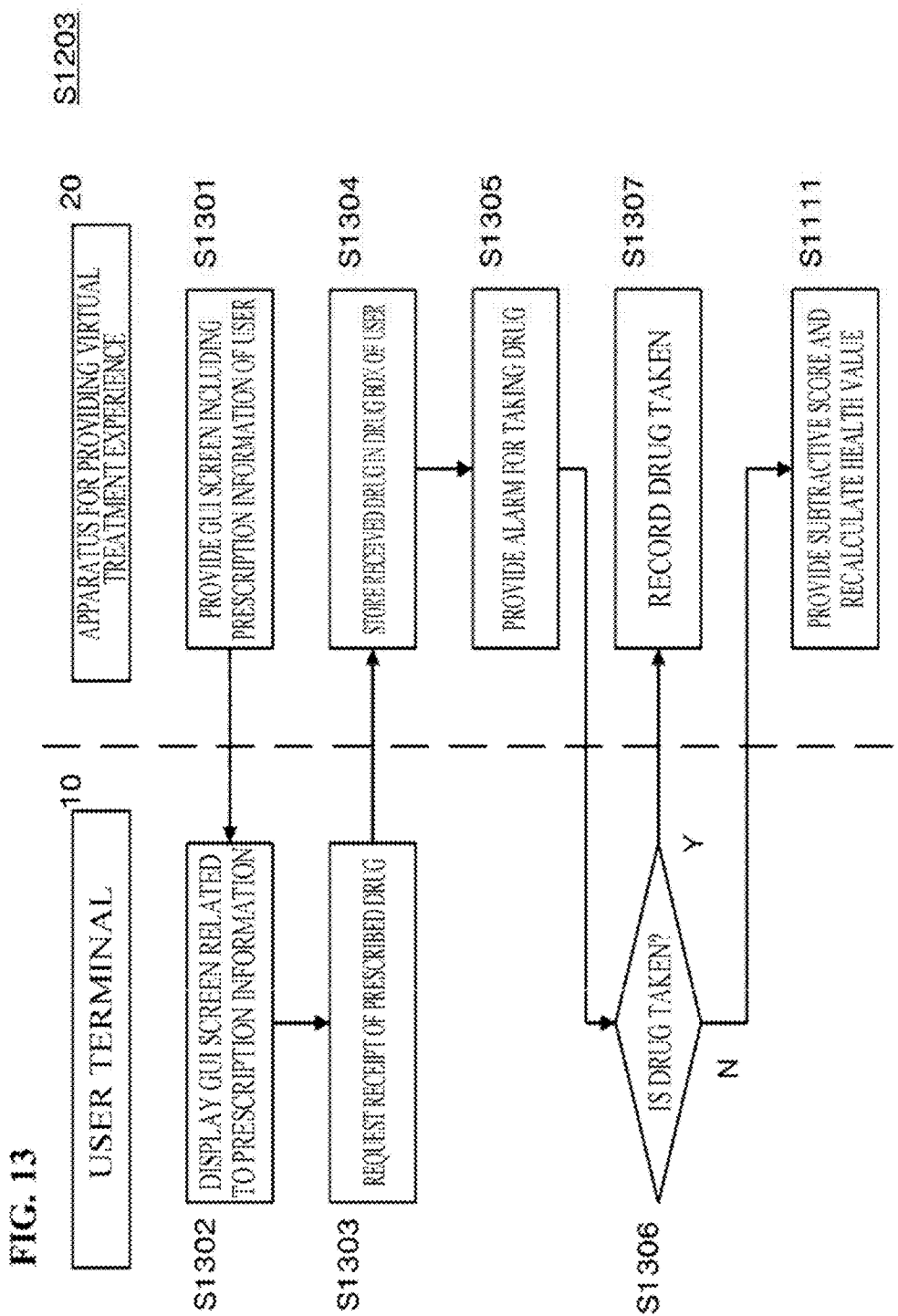
FIG. 13 is a diagram showing an example of a virtual activity scenario corresponding to taking a drug shown in FIG. 12.

FIG. 13 is a diagram showing an example of a virtual activity scenario corresponding to taking a drug shown in FIG. 12.

Referring to FIG. 13, in the present embodiment, when a virtual activity selected in a user terminal 10 is taking a drug, the apparatus 20 for providing a virtual treatment experience may inquire about prescription information of a user and provide a GUI screen including obtained prescription information of the user to the user terminal 10 (S1301).

Subsequently, the user terminal 10 may display the GUI screen including the prescription information (S1302) and request receipt of a prescribed drug from the apparatus 20 for providing a virtual treatment experience (S1303).

Then, the apparatus 20 for providing a virtual treatment experience may process a receipt of the prescribed drug and store the received drug in a drug box of the user (S1304) and provide an alarm for taking a drug to the user terminal 10 at time to take the drug (S1305).

Subsequently, when the user terminal 10 performs taking a drug in response to the alarm for taking a drug (S1306, Y), the apparatus 20 for providing a virtual treatment experience may record drugs-taken information of the user (S1307).

Meanwhile, when the user terminal 10 does not perform taking a drug in spite of the alarm for taking a drug (S1306, N), the apparatus 20 for providing a virtual treatment experience may provide a subtractive score to the user and recalculate a health value (S1111).

Figure 14:
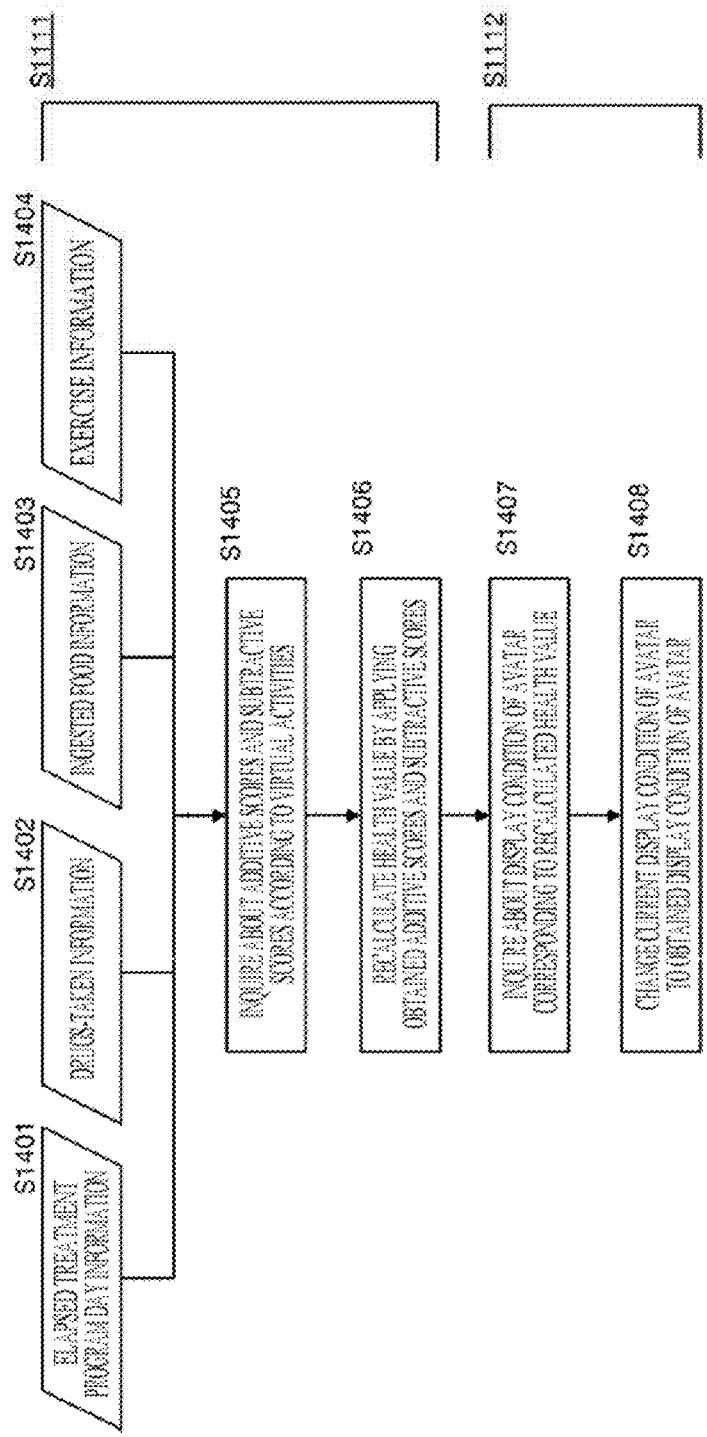
FIG. 14 is a diagram showing an example of a detailed configuration of a process of recalculating a health value and a process of changing a display condition of an avatar shown in FIG. 11.

FIG. 14 is a diagram showing an example of a detailed configuration of a process of recalculating a health value and a process of changing a display condition of an avatar shown in FIG. 11.

Referring to FIG. 14, the apparatus 20 for providing a virtual treatment experience may inquire about additive scores and subtractive scores according to virtual activities (S1405) using elapsed treatment program day information (S1401), drugs-taken information (S1402), ingested food information (S1403), exercise information (S1404), and so on.

After that, the apparatus 20 for providing a virtual treatment experience may recalculate the health value by applying the obtained additive scores and subtractive scores to a health value set according to the elapsed treatment program days (S1406).

Subsequently, the apparatus 20 for providing a virtual treatment experience may inquire about a display condition of the avatar corresponding to the recalculated health value (S1407) and may change the current display condition of the avatar to the obtained display condition of the avatar and display the changed display condition (S1408). Here, the display condition of the avatar may be set to vary over a period of the treatment program and determined by a basic value of a health value set according to a date.

Thus far, the present invention has been described with reference to exemplary embodiments thereof. It will be understood by those of ordinary skill in the art to which the present invention pertains that various changes and other equivalent embodiments can be made from the exemplary embodiments without departing from the spirit and scope of the invention. Therefore, the disclosed embodiments are to be construed as illustrative rather than limiting, and all differences present within equivalents should be construed as being included in the present invention.

An apparatus and method according to the present invention can be implemented as a computer-readable code on a computer-readable recording medium. The computer-readable recording medium includes any kinds of recording devices in which data readable by a computer system is stored. Examples of the recording medium are a read only memory (ROM), a random access memory (RAM), a compact disc (CD)-ROM, a magnetic tape, a floppy disk, an optical data storage, etc., and also include implementation in the form of carrier wave (e.g., transmission through the Internet). In addition, the computer-readable medium may be distributed to computer systems connected through a network so that the computer readable code is stored and executed in a distributed manner.

The invention claimed is:

1. A method of providing a virtual treatment experience, the method comprising:
   a first operation of acquiring medical information including disease name and blood value of a patient and treatment information including treatment program information and prescription information;
   a second operation of calculating health value information by quantifying a current health condition of the patient based on the medical information of the patient, and selecting a display image of an avatar corresponding to the calculated health value information;
   a third operation of proceeding with a virtual activity according to a manipulation command from a user terminal of the patient such that the user terminal displays the avatar performing the virtual activity, and inquiring an additive score and a subtractive score according to a result of proceeding with the virtual activity;
   a fourth operation of calculating a heath value of the patient using health value information set according to a number of days for which the treatment program has been applied and the inquired additive score and subtractive score; and
   a fifth operation of changing the display image of the avatar according to the calculated health value of the patient.

2. The method of claim 1, further comprising, before the first operation, setting health values according to numbers of days for which a treatment period of the treatment program has been elapsed, generating display images of the avatar to which physical side effects produced by progress of the treatment program have been applied in stages, and setting the generated display images of the avatar differently according to health value ranges.

3. The method of claim 1, wherein the second operation further includes setting a virtual treatment experience service period to be identical to a treatment period of the treatment program based on the treatment information of the patient, and then starting the treatment program.

4. The method of claim 1, wherein the third operation further includes providing helping words describing effects of the virtual activity on treatment.

5. The method of claim 1, wherein the virtual activity is one of taking a drug, cooking, walking, crop cultivation, exercising, shopping, and a community activity.

6. The method of claim 1, wherein the prescription information includes information on a kind and dosing time of a drug actually prescribed at a hospital,
   an alarm function is provided for the avatar to take the drug when a preset time arrives according to the dosing time information, and
   when the avatar does not take the drug at the preset time, the health value of the patient is recalculated to change the display image of the avatar.

7. The method of claim 1, further comprising operating in conjunction with another user terminal connected through a communication network, displaying an avatar of the other user terminal in a virtual space, and providing a community activity with the other user terminal.

8. An apparatus for providing a virtual treatment experience, the apparatus comprising:
   a patient information manager configured to acquire medical information including disease name and blood value of a patient and treatment information including treatment program information and prescription information;
   a virtual activity provider configured to proceed with a virtual activity according to a manipulation command from a user terminal of the patient such that the user terminal displays the avatar performing the virtual activity, and inquire an additive score and a subtractive score according to a result of proceeding with the virtual activity; and
   a controller configured to calculate health value information by quantifying a current health condition of the patient based on the blood value of the patient, select a first display image of an avatar corresponding to the calculated health value information, recalculate the heath value information of the patient using health value information set according to a number of days for which the treatment program has been applied and the inquired additive score and subtractive score, and change the first display image of the avatar to a second display image according to the recalculated health value information of the patient.

9. The apparatus of claim 8, further comprising a database configured to store the acquired medical information and treatment information, the health value information set according to the number of days for which the treatment program has been applied, display images of the avatar generated by applying physical side effects produced by progress of the treatment program in stages, and matching information obtained by matching the generated display images of the avatar to health value ranges.

10. The apparatus of claim 9, wherein the virtual activity is one of taking a drug, cooking, walking, crop cultivation, exercising, shopping, and a community activity, and
    the virtual activity provider separately provides additive scores when the avatar takes a drug, eats designated food helpful for treatment, goes for a walk, and does exercise.

11. The apparatus of claim 8, wherein the virtual activity provider operates in conjunction with another user terminal connected through a communication network, displays an avatar of the other user terminal in a virtual space, and provides a community activity with the other user terminal.

12. The apparatus of claim 11, wherein, when providing the community activity, the virtual activity provider provides a message transmission function and a chatting function to the avatar of the other user terminal existing in the virtual space.

13. The apparatus of claim 9, wherein the controller sets a virtual treatment experience service period to be identical to a treatment period of the treatment program based on the treatment information of the patient, and starts the treatment program and counts a number of days for which the treatment program has been applied upon selecting the first display image of the avatar.

14. The apparatus of claim 8, wherein the prescription information includes information on a kind and dosing time of a drug actually prescribed at a hospital, and
    the controller provides an alarm function for the avatar to take the drug when a preset time arrives according to the dosing time information, and recalculates the health value of the patient and changes the second display image of the avatar to a third display image when the avatar does not take the drug at the preset time.

* * * * *